United States Patent
Forsell (10) Patent No.: US 11,273,063 B2
(45) Date of Patent: *Mar. 15, 2022

(54) FASTENING DEVICE, IMPLANT DEVICE, LOCKING METHOD, AND OPERATION METHOD

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 302 days.

This patent is subject to a terminal disclaimer.

(21) Appl. No.: 16/504,461

(22) Filed: Jul. 8, 2019

(65) Prior Publication Data
US 2020/0000614 A1    Jan. 2, 2020

Related U.S. Application Data

(63) Continuation of application No. 14/635,134, filed on Mar. 2, 2015, now Pat. No. 10,342,689, which is a
(Continued)

(30) Foreign Application Priority Data
Oct. 29, 2009   (SE) .................................... 0901391-3

(51) Int. Cl.
*A61F 5/00*   (2006.01)
*A61B 17/12*  (2006.01)
*A61B 17/00*  (2006.01)

(52) U.S. Cl.
CPC ...... *A61F 5/0066* (2013.01); *A61B 17/12009* (2013.01); *A61F 5/0053* (2013.01); *A61B 2017/00535* (2013.01); *A61F 5/0056* (2013.01)

(58) Field of Classification Search
None
See application file for complete search history.

(56) References Cited

U.S. PATENT DOCUMENTS

5,074,868 A * 12/1991 Kuzmak ................. A61F 5/003
                                                        606/157
5,601,604 A *  2/1997 Vincent .................. A61F 5/003
                                                        606/216
(Continued)

*Primary Examiner* — Shaun L David (57) ABSTRACT

The invention relates to a fastening device for implant device, the fastening device comprising at least two fastening sections, where a first fastening section is arranged with a through hole, a second fastening section is arranged with a protruding part, and where said protruding part is in place in said through hole in a fastening device locking state, where the protruding part on the second fastening section is arranged with a through channel having an inlet and an outlet, said through channel being arranged to receive an implant device feed member, said inlet and outlet being accessible from the exterior of the fastening device in said fastening device locking state, wherein the first fastening section is securely locked to the second fastening section when, in said fastening device locking state, said implant device feed member is in place in the through channel and protrudes from both the inlet and the outlet of said through channel. The invention further relates to an implant device comprising a fastening device, and a method for securely locking a first fastening section of a fastening device for an implant device to a second section of a fastening device for an implant device.

20 Claims, 8 Drawing Sheets

Related U.S. Application Data continuation of application No. 13/384,498, filed as application No. PCT/SE2010/051177 on Oct. 29, 2010, now Pat. No. 8,968,344.

(60) Provisional application No. 61/255,991, filed on Oct. 9, 2009.

(56) References Cited

U.S. PATENT DOCUMENTS

| | | | | |
|---|---|---|---|---|
| 6,966,875 B1* | 11/2005 | Longobardi | | A61F 5/005 600/31 |
| 7,824,422 B2* | 11/2010 | Benchetrit | | A61F 5/0066 606/157 |
| 2003/0120288 A1* | 6/2003 | Benchetrit | | A61F 5/0056 606/151 |
| 2003/0158564 A1* | 8/2003 | Benchetrit | | A61F 5/0066 606/151 |
| 2004/0158272 A1* | 8/2004 | Hofle | | A61F 5/005 606/192 |
| 2004/0267288 A1* | 12/2004 | Byrum | | A61F 5/0066 606/151 |
| 2004/0267292 A1* | 12/2004 | Byrum | | A61F 5/003 606/157 |
| 2004/0267293 A1* | 12/2004 | Byrum | | A61F 5/0056 606/157 |
| 2005/0002984 A1* | 1/2005 | Byrum | | A61F 5/0056 424/423 |
| 2007/0004963 A1* | 1/2007 | Benchetrit | | A61F 5/0056 600/37 |
| 2008/0097487 A1* | 4/2008 | Pool | | A61F 5/003 606/151 |
| 2008/0146869 A1* | 6/2008 | Chow | | A61F 5/005 600/37 |
| 2008/0287976 A1* | 11/2008 | Weaner | | A61F 5/0056 606/157 |
| 2009/0240269 A1* | 9/2009 | Denis | | A61F 5/0066 606/157 |
| 2011/0040313 A1* | 2/2011 | Dlugos, Jr | | A61F 5/003 606/157 |
| 2013/0035544 A1* | 2/2013 | Pool | | A61F 5/0059 600/37 |

* cited by examiner

FASTENING DEVICE, IMPLANT DEVICE, LOCKING METHOD, AND OPERATION METHOD

This application is a continuation of U.S. patent application Ser. No. 14/635,134, now U.S. Pat. No. 10,342,689, which is a continuation of U.S. patent application Ser. No. 13/384,498, filed on Jan. 17, 2012, now U.S. Pat. No. 8,698,344, which is the U.S. national phase of International Application No. PCT/SE2010/051177, filed 29 Oct. 2010, which designated the U.S. and claims the benefit of U.S. Provisional Application No. 61/255,991, filed 29 Oct. 2009, and which claims priority to Swedish Application No.: 0901391-3, filed 29 Oct. 2009, the entire contents of each of which are hereby incorporated by reference.

TECHNICAL FIELD OF THE INVENTION

The present invention relates to a fastening device for an implant device as stated in the preamble of claim 1.

TECHNICAL BACKGROUND

Implant devices are devices that are adapted for being placed in e.g. human bodies or animals, and that e.g. replace body parts that have been damaged or removed e.g. due to cancer.

In order to keep the implant device in place so that it does not move freely within e.g. a human body cavity, it is known to fasten the implant device in position using a fastening device. A known fastening device is a band type device having two ends, where a first end has a hole and a second end has a protruding part arranged to be placed in said hole in order to lock the two ends of the band device together after having been looped around an implant device and a body part such as an intestine, thereby fastening the implant device in place. In order for the band ends not to be separated when e.g. a person carrying the implant moves around, the protruding part is of flexible material and has a ball shaped outer end of somewhat larger cross-section than the diameter of the hole, whereby the ball shaped end is elastically deformed when pushed through the hole and regains its shape when leaving the hole, thus keeping the band ends locked to each other.

SUMMARY OF THE INVENTION

The problem of keeping an implant in place so that it does not move freely is solved according to the invention: by a fastening device for an implant device as stated in the characterizing portion of claim 1.

By that the fastening device, implant device, locking method, and operation method as stated in the characterizing portions of claims 1, comprise the characteristic features that the fastening device comprises at least a first fastening section with a hole, and a second fastening section having a protruding part being arranged with a through channel having an inlet and an outlet, where said inlet and outlet are accessible from the exterior of the fastening device in a listening device locking state, and where an implant device feed member is in place in the through channel and protrudes from both the inlet and the outlet of said through channel in the fastening device locking state, the advantage of obtaining a secure locking of the first fastening section to the second fastening section is achieved.

Further preferred exemplary embodiments are defined in the dependent claims.

In one embodiment, the first fastening section has e.g. a cylindrical, tubular or band shaped cross-section.

In one embodiment, the first fastening section has a tubular cross-section, and that the through hole is arranged at least through one wall of the tubular first fastening section.

In one embodiment, the second fastening section has e.g. a cylindrical, tubular or band shaped cross-section.

In one embodiment, the first and the second fastening sections are arranged on the same fastening unit.

In one embodiment, the fastening unit is attached to the implant device.

In one embodiment, the implant device feed member is attached to the fastening unit.

In one embodiment, the first and the second fastening sections are arranged on separate fastening units.

In one embodiment, the at least one of the fastening units is attached to the implant device.

In one embodiment, the implant device feed member is attached) a fastening unit.

In one embodiment, the inlet and the outlet of the through channel arranged in the protruding part on the second fastening section are arranged on the same side of the first fastening section in the fastening device locking state.

In one embodiment, the inlet and the outlet of the through channel arranged in the protruding part on the second listening section are arranged on different sides of the first fastening section in the fastening device locking state.

In one embodiment, the outlet of the through channel arranged in the protruding part on the second fastening section is arranged to connect to an inlet of a through hole arranged in the second fastening section, wherein the inlet of the through channel arranged in the protruding part on the second fastening section and the outlet of the through hole in the second fastening section are arranged on different sides of the first fastening section in the fastening device locking state.

In one embodiment, the inlet and the outlet of the through channel arranged in the protruding part on the second fastening section are arranged on opposite sides of the first fastening section in the fastening device locking state.

In one embodiment, the inlet and the outlet of the through channel arranged in the protruding part on the second fastening section are arranged adjacent the surface of the first fastening section in the fastening device locking state.

In one embodiment, the protruding pan arranged on the second fastening section is arranged to protrude substantially axially from one end of the second fastening section.

In one embodiment, the inlet and the outlet of the through channel arranged in the protruding part on the second fastening section are arranged on different sides of the second fastening section.

In one embodiment, the protruding part arranged on the second fastening section is arranged to protrude substantially perpendicular to the longitudinal axis of the second fastening section, and from one end of the second fastening section.

In one embodiment, the protruding part arranged on the second fastening section is arranged to protrude substantially perpendicular to the longitudinal axis of the second fastening section.

In one embodiment, the protruding part arranged on the second fastening section is arranged adjacent to one end of the second fastening section.

In one embodiment, the through hole arranged in the first fastening section is arranged at an angle to the longitudinal axis of the first fastening section.

In one embodiment, the protruding part arranged on the second fastening section is arranged at an angle to the longitudinal axis of the second fastening section.

In one embodiment, the through hole arranged in the first fastening section is arranged substantially perpendicular to the longitudinal axis of the first fastening section.

In one embodiment, the implant device feed member is arranged to feed hydraulic fluid, pneumatic fluid, or electrical energy or electrical signals between the implant device and a remote unit.

In one embodiment, the implant device feed member is arranged to feed hydraulic fluid, pneumatic fluid, or electrical energy or electrical signals to the implant device.

In one embodiment, the implant device feed member is arranged to feed hydraulic fluid, pneumatic fluid, or electrical energy or electrical signals from the implant device.

In one embodiment, the first fastening section is detachably securely locked to the second fastening section when said implant device feed member is in place in the through channel and protrudes from both the inlet and the outlet of said through channel.

In one embodiment, the implant device feed member is attached to the implant device.

In one embodiment, the implant device feed member is detachably attached to the implant device.

In one embodiment, the protruding part is an integrated part of the second fastening section.

In one embodiment, the implant device is arranged to be fastened around a body part or another implanted device or member.

In one embodiment, the first fastening section is arranged with more than one through hole in order to be able to lock the fastening device in more than one fastening device locking state.

In one embodiment, the first fastening section is arranged with more than one through hole, and in that the second fastening section is arranged with more than one protruding part in order to be able to lock the fastening device in more than one fastening device locking state, i.e. the fastening device is adapted to create two or more locking positions, said fastening device comprising two or more protruding parts and two or more through going holes wherein a first through going hole is placed more distal to the second or more through wing hole to include anyone of the protruding parts inside said first through going hole, thus creating, two or more locking position.

In one embodiment, the implant device is arranged to be fastened around at least one of a stomach or divided part of the stomach, an intestine, a closing sphincter and other part of the food passageway.

In one embodiment, the implant device is arranged to be fastened around at least one of an urethra and other part of the urinary tract.

In one embodiment, the implant device is arranged to be fastened around a blood vessel or heart.

In one embodiment, the implant device is arranged to be fastened around a vas deferens or uterine tube.

In one embodiment, the implantable implant device comprises a restriction device and wherein the fastening device is adapted to create a closed loop by fastening said restriction device.

In one embodiment, the implant device comprising at least two implant device parts placed remote from each other, and wherein said implant device feed member is adapted to be connected to at least said two parts, when said implant is implanted in a mammal body.

In one embodiment, at least one of said implant device parts comprise an internal energy source.

In one embodiment, at least one of said implant device parts comprises an internal wireless energy receiver adapted to receive wireless energy for supplying energy to any of the energy consuming parts of said implant device.

In one embodiment, at least one of said implant device parts comprises a pump.

In one embodiment, at least one of said implant device parts comprises a motor.

In one embodiment, said implant device is an adjustable hydraulically implant device, comprising a restriction device, and a pump for moving hydraulic fluid to and from said restriction device, wherein said fastening device is adapted to fasten said first and second fastening sections included in said restriction device into a closed loop and wherein said restriction device and said pump is hydraulically connected by a hydraulic tube, wherein said tube comprising the implant feed member.

The invention also relates to a fastening device, wherein said implant device is an adjustable electrically powered implant device, comprising a restriction device, and a power supply for powering an adjustment of said restriction device, wherein said fastening device is adapted to fasten said first and second fastening sections included in said restriction device into a closed loop and wherein said restriction device and said power supply is electrically connected by a electric cable, wherein said cable comprising the implant feed member In one embodiment, the invention further relates to a method for securely locking a first fastening section of a fastening device for an implant device to a second fastening section of a fastening device for an implant device, the fastening device comprising at least two fastening sections, where the first fastening section is arranged with a through hole and the second fastening section is arranged with a protruding part, and where a fastening device locking state is defined by said protruding part being placed in place in said through hole, where the method comprises the steps of:
 arranging, on the protruding part on the second fastening section, a through channel having an inlet and an outlet, said through channel being arranged to receive an implant device feed member, said inlet and outlet being accessible from the exterior of the fastening device in said fastening device locking state,
 placing said implant device feed member in the through channel, and
 securely locking the film fastening section to the second fastening section by arranging, in said fastening device locking state, said implant device feed member to protrude from both the inlet and the outlet of said through channel.

In one embodiment, the invention also relates to an operation method for implanting a medical implant comprising a fastening device according to claim 1, the method comprising the steps of
 inserting a needle or tube-like instrument into a cavity of said mammal patient;
 inflating said cavity by introducing a fluid through said needle or tube-like instrument and thereby expanding said cavity;
 placing at least two laparoscopic trocars in said cavity;
 inserting a camera through one of said laparoscopic trocars into said cavity;
 inserting at least one dissecting tool through one of said at least two laparoscopic trocars;
 dissecting an area of the body;

placing the implant with the fastening device in the dissected area;

locking a first fastening section of a fastening device for the implant device to a second fastening section of the fastening device, the fastening device comprising at least two fastening sections, where the first fastening section is arranged with a through hole and the second listening section is arranged with a protruding part, and where a fastening device locking state is defined by said protruding part being placed in place in said through hole, arranging, on the protruding part on the second fastening section, a through channel having an inlet and an outlet, said through channel being arranged to receive an implant device feed member, said inlet and outlet being accessible from the exterior of the fastening device in said fastening device locking state, placing said implant device feed member in the through channel, and securely locking the first fastening section to the second fastening section by arranging, in said fastening device locking state, said implant device feed member to protrude from both the inlet and the outlet of said through channel, In one embodiment, the invention also relates to an for implanting a medical implant comprising a fastening device according to claim 1, the method comprising the steps of cutting the skin of said human patient;

dissecting an area of body;

placing the implant in the dissected area;

locking a first fastening section of a fastening device for the implant device to a second fastening section of the fastening device, the fastening device comprising at least two fastening sections, where the first fastening section is arranged with a through hole and the second fastening section is arranged with a protruding part, and where a fastening device locking state is defined by said protruding part being placed in place in said through hole, arranging, on the protruding part on the second fastening section, a through channel having an inlet and an outlet, said through channel being arranged to receive an implant device feed member, said inlet and outlet being accessible from the exterior of the fastening device in said fastening device locking state, placing said implant device feed member in the through channel, and securely locking the first fastening section to the second fastening section by arranging, in said fastening device locking state, said implant device feed member to protrude from both the inlet and the outlet of said through channel.

In one embodiment, the invention also relates to a method of treating a mammal patient according to any one of above described operation methods, thriller comprising the step of withdrawing the instruments.

In one embodiment, the invention also relates to a method of treating a mammal patient according to any one of above described operation methods, further comprising the stop of closing the skin using sutures or staples.

In one embodiment, the invention also relates to a method of treating a mammal patient according to any one of above described operation methods, wherein the step of dissecting includes dissecting an area of the abdomen or thorax or retroperitoneal space or pelvic region, comprising, dissecting an area of at least one of the following organs esophagus, stomach, intestine, colon, rectum, anus, anal spincter, cardia sphincter, pylori sphincter, urethra, ureter, urine bladder, vas deferens, uterine tube, blood vessel, and heart.

In one embodiment, the invention also relates to a method of treating a mammal patient according to any one of above described operation methods, wherein the implantable device comprise a restriction device and the fastening device is adapted to create a closed loop by fastening said restriction device, wherein the method comprising the step of fastening said fastening device creating a closed loop.

In further embodiments, the invention also relates to an implant device comprising a fastening device as described in any of the above embodiments above, or possible combinations thereof.

Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

DESCRIPTION OF PREFERRED EMBODIMENTS

Briefly described, the present invention provides a solution for enabling an easy and i.e. 100%, reversible way of keeping an implant in place so that it does not move freely, by providing and placing a fastening device for an implant device into e.g. a body of a patient, where the "patient" is a living creature such as e.g. a human or an animal.

Figure 1:
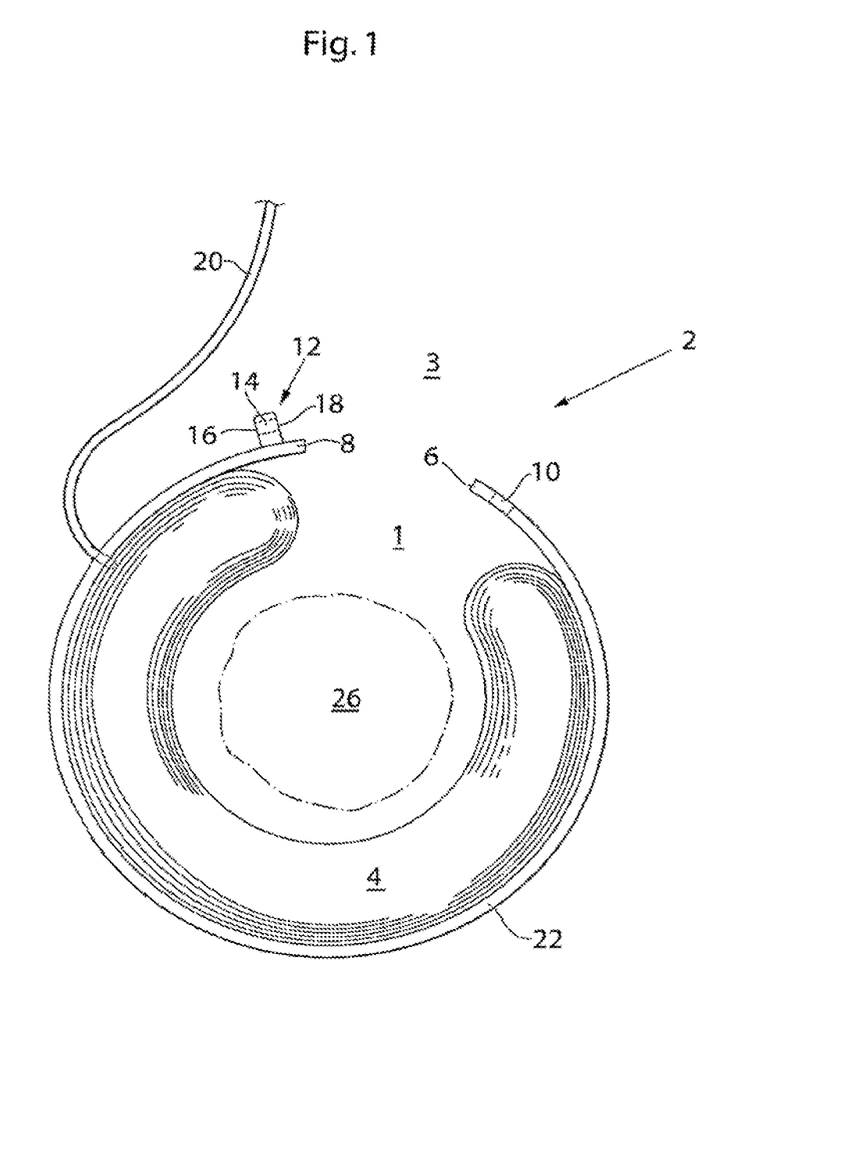
FIG. 1 shows schematically a fastening device for an implant device according to one exemplary embodiment of the invention.
Figure 2:
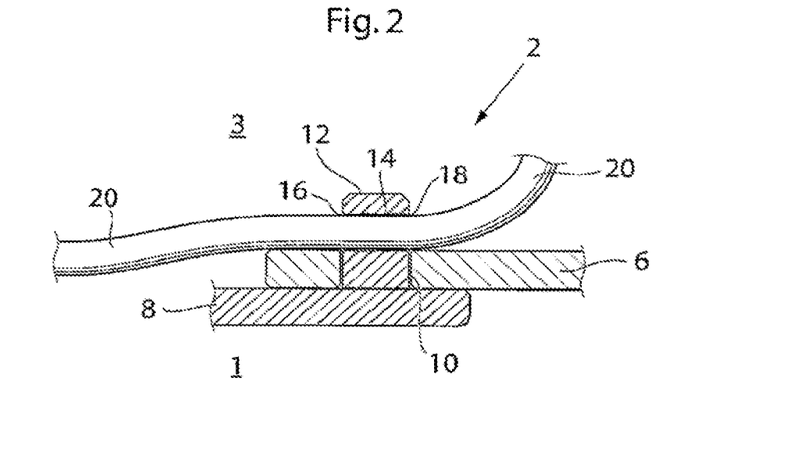
FIG. 2 shows schematically fastening sections of a fastening, device according to one exemplary embodiment of the invention.

The invention is now described, by way of example, with reference to the accompanying drawings, in which:

FIG. 1 shows schematically a fastening device 2 for an implant device 4 according to one exemplary embodiment of the invention, where the fastening device 2 comprises at least two fastening sections 6, 8 (only two fastening sections are shown in the figure), where a first fastening section 6 is arranged with a through hole 10, a second fastening section 8 is arranged with a protruding part 12, and where said protruding part 12 is in place in said through hole 10 in a fastening device locking state (for the fastening device locking state, see FIG. 2. FIG. 1 shows an unlocked fastening device state). As can be seen from the FIG. 1, the protruding part 12 on the second fastening section 8 is arranged with a through channel 14 having an inlet 16 and an outlet 18, said through channel 14 being arranged to receive an implant device feed member 20, said inlet 16 and outlet 18 being accessible from the exterior 1, 3 of the fastening device 2 in said fastening device locking state, wherein the first fastening section 6 is securely locked to the second fastening section 8 when, in said fastening device locking state, said implant device feed member 20 is in place in the through channel 14 and protrudes from both the inlet 16 and the outlet 18 of said through channel 14.

Said through channel 14 may be of any length, i.e. if the protruding part 12 is very thin, said through channel 14 could be similar to a hole.

Figure 8:
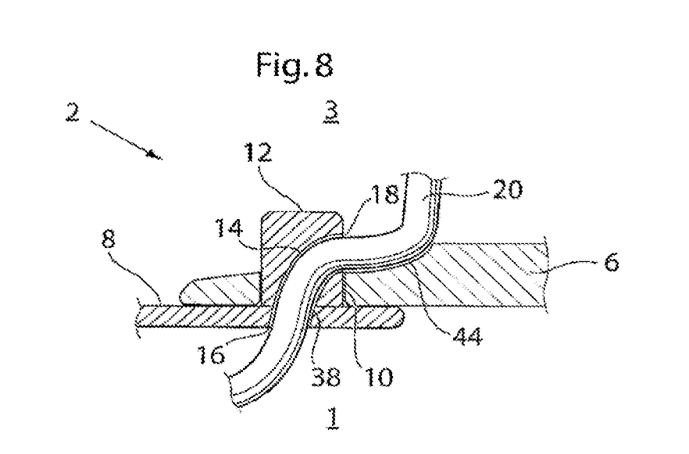
FIG. 8 shows schematically fastening sections of a fastening device according to yet another exemplary embodiment of the invention.

Said inlet 16 and outlet 18 are accessible from the exterior of the fastening device 2 in said fastening device locking state, i.e. said inlet 16 and/or outlet 18 may be accessible from one or more sides of the fastening device 2 in said fastening device locking state, e.g. from one of or from some of the following sides: the outer side, the inner side, or any other side not belonging to the outer side and the inner side, of the fastening device 2, see e.g. FIG. 8 showing an embodiment where said inlet 16 is accessible from the exterior of the fastening device 2 by being accessible from the inner side 1 of the fastening device 2 and where said outlet 18 is accessible from the exterior of the fastening device 2 by being accessible from the outer side 3 of the fastening device 2.

The first fastening section 6 of the fastening device 2, and the second fastening section 8 of the fastening device 2, may have any cross-section, e.g. a cylindrical, tubular or band shaped cross-section, where a band shaped cross-section is shown in the figure for both the first fastening section 6 and the second fastening section 8, and where the cross-section of the first fastening section 6 does not have to be the same as the cross-section of the second fastening section 8.

The first and the second fastening sections 6, 8 may be arranged on the same fastening unit or on separate fastening units, where an embodiment where the first and the second fastening sections 6, 8 are arranged on the same fastening unit 22, is shown in the figure.

None or at least one of the fastening units may be attached to the implant device 4, and the implant device feed member 20 may be or not be attached to a fastening unit, where an embodiment where no fastening unit 22 is attached to the implant device 4 by attachment means, e.g. by chemical or mechanical means such as adhesive or suturing, and where the implant device feed member 20 is not attached to a fastening unit 22, is shown in the figure.

The inlet 16 and the outlet 18 of the through channel 14 arranged in the protruding part 12 on the second fastening section 8 may be arranged on the same side of the first fastening section 6 in the fastening device locking state, or on different sides of the first fastening section 6 in the fastening device locking state, where an embodiment where the inlet 16 and the outlet 18 of the through channel 14 arranged in the protruding part 12 on the second fastening section 8 is arranged on the same side of the first fastening section 6 in the fastening device locking state, is shown in the figure.

It could also be possible to arrange the outlet of the through channel arranged in the protruding part on the second fastening section to connect to an inlet of a through hole arranged in the second fastening section, wherein the inlet of the through channel arranged in the protruding part on the second fastening section and the outlet of the through hole in the second fastening section are arranged on different sides of the first fastening section in the fastening device locking state, whereby the inlet and the outlet of the through channel arranged in the protruding part on the second fastening section might be arranged on opposite sides of the first fastening section in the fastening device locking state (not shown in the figure).

As shown in both the embodiment according to FIG. 1, and being more clearly visible from FIG. 2, it is preferable to arrange the inlet 16 and/or the outlet 18 of the through channel 14 arranged in the protruding part 12 on the second fastening section 21 adjacent to the surface of the first fastening section 6 in the fastening device locking state for minimizing any play in the locking device between the first fastening section 6 and the second fastening section 8, but it is also possible to arrange the inlet 16 and the outlet 18 of the through channel 14 arranged in the protruding part. 12 on the second fastening section 8 somewhat distanced from the surface of the first fastening section 6 in the fastening device locking state, whereby some play may occur in the locking device between the first fastening section 6 and the second fastening section 8.

The first fastening section 6 is preferably detachably securely locked to the second fastening section 8 when said implant device feed member 20 is in place in the through channel 14 and protrudes from both the inlet 16 and the outlet 18 of said through channel 14, by that it is possible to remove the implant device feed member 20 from the through channel 14, where after it is possible to detach the first fastening section 6 from the second fastening section 8, this without any substantial effort and without having to deform any parts of the fastening device 2.

The implant device feed member 20 may or may not be detachably or non-detachably attached to the implant device 4.

The implant device feed member 20 may be arranged to feed hydraulic fluid, pneumatic fluid, or electrical energy or electrical signals between the implant device 4 and a remote unit 24, e.g. that the implant device feed member 20 is arranged to feed hydraulic fluid, pneumatic fluid, or electrical energy or electrical signals to and/or from the implant device 4.

As can be seen from the figure, the implant device 4 may be arranged to be fastened around a body part or another implanted device or member 26. Said body part may e.g. be at least one of a stomach or divided part of the stomach, an intestine, a closing sphincter and other part of the food passageway. Said body part may e.g. be at least one of an urethra and other part of the urinary tract. Said body part may e.g. be a blood vessel or heart. Said body part may e.g. be a vas deferens or uterine tube.

FIG. 2 shows schematically fastening sections 6, 8 of a fastening device 2 according to one exemplary embodiment of the invention, where a first fastening section 6 is arranged with a through bole 10, a second fastening section 8 is arranged with a protruding part 12, and where said protruding part 12 is in place in said through hole 10 in a fastening device locking state (FIG. 2 shows an locked fastening device state). As can be seen from the figure, the protruding part 12 on the second fastening section 8 is arranged with a through channel 14 having an inlet 16 and an outlet 18, said through channel 14 being arranged to receive an implant device feed member 20, said inlet 16 and outlet 18 being accessible from the exterior 1, 3 of the fastening device 2 in said fastening device locking state, wherein the first fastening section 6 is securely locked to the second fastening section 14 when, in shown fastening device locking state, said implant device feed member 20 is in place in the through channel 14 and protrudes from both the inlet 16 and the outlet 18 of said through channel 14.

According to the embodiment shown in FIG. 2, which is a detailed partial cross-section of the embodiment shown in FIG. 1, band shaped cross-section is shown for both the first fastening section 6 and the second fastening section 8, and both the first and the second fastening sections 6, 8 are arranged on the same fastening unit 22, and the inlet 16 and the outlet 18 of the through channel 14 arranged in the protruding part 12 on the second fastening section 8 are arranged on the same side of the first fastening section 6 in the fastening device locking state.

As shown in both the embodiment according to FIG. 1, and being more clearly visible from FIG. 2, it is preferable to arrange the inlet 16 and/or the outlet 18 (in this embodiment both the inlet 16 and the outlet 16) of the through channel 14 arranged in the protruding part 12 on the second fastening section 8 adjacent to the surface of the first fastening section 6 in the fastening device locking state for minimizing any play in the locking device between the first fastening section 6 and the second fastening section 8.

Figure 3:
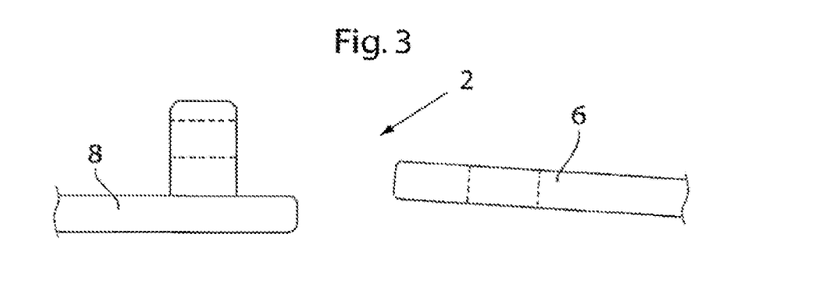
FIG. 3 shows schematically fastening sections of a fastening device according to another exemplary embodiment of the invention.

FIG. 3 shows schematically fastening sections 6, 8 of a fastening device 2 according to another exemplary embodiment of the invention, which embodiment differs from the one described in FIG. 2, in that a cylindrical shaped cross-section is shown for both the first fastening section 6 and the second fastening section 8.

Figure 4:
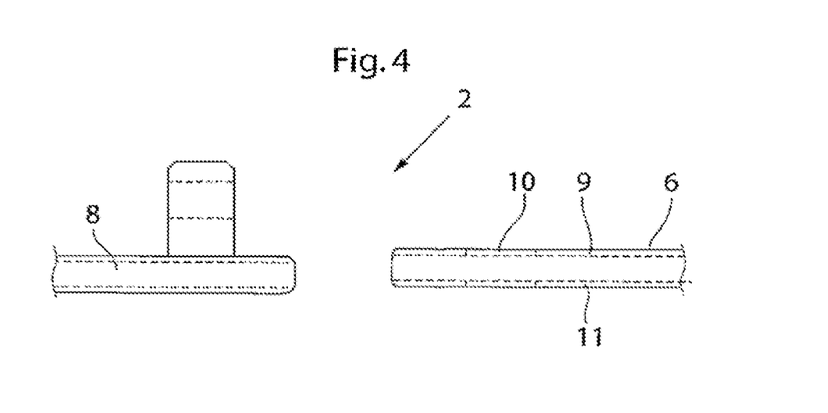
FIG. 4 shows schematically fastening sections of a fastening device according to yet another exemplary embodiment of the invention.

FIG. 4 shows schematically fastening sections 6, 8 of a fastening device 2 according to yet another exemplary embodiment of the invention, which embodiment differs from the one described in FIG. 2, in that a tubular cross-section is shown for both the first fastening section 6 and the second fastening section 8. As is shown in the figure, the through hole 10 is to at least through one wall 9, 11 of the tubular first fastening section 6.

Figure 5:
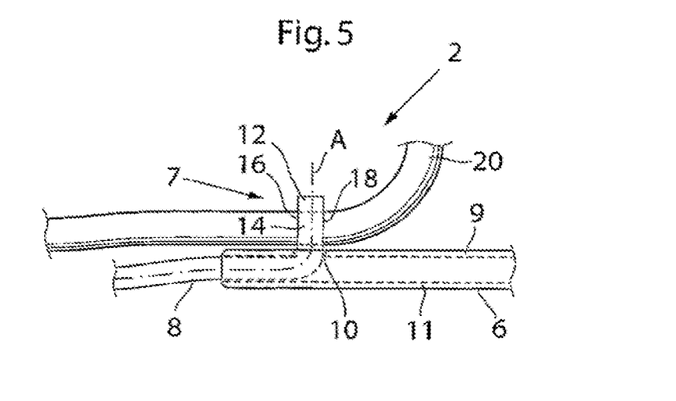
FIG. 5 shows schematically fastening sections of a fastening device according to yet another exemplary embodiment of the invention.

FIG. 5 shows schematically fastening sections 6, 8 of a fastening device 2 according to yet another exemplary embodiment of the invention, which embodiment differs from the one described in FIG. 4, in that a tubular cross-section is shown for the first fastening section 6 and a cylindrical cross-section is shown for the second fastening section 8. As is shown in the figure, the through hole 10 is arranged at least through one wall 9, 11 of the tubular first fastening section 6, and the protruding part 12 arranged on the second fastening section 8 is arranged to protrude substantially axially A from one end 7 of the second fastening section 8.

As can be seen from the figure, in this embodiment the inlet 16 and the outlet 18 of the through channel 14 arranged in the protruding part 12 on the second fastening section 8 are arranged on opposite sides of the second fastening section.

Figure 6:
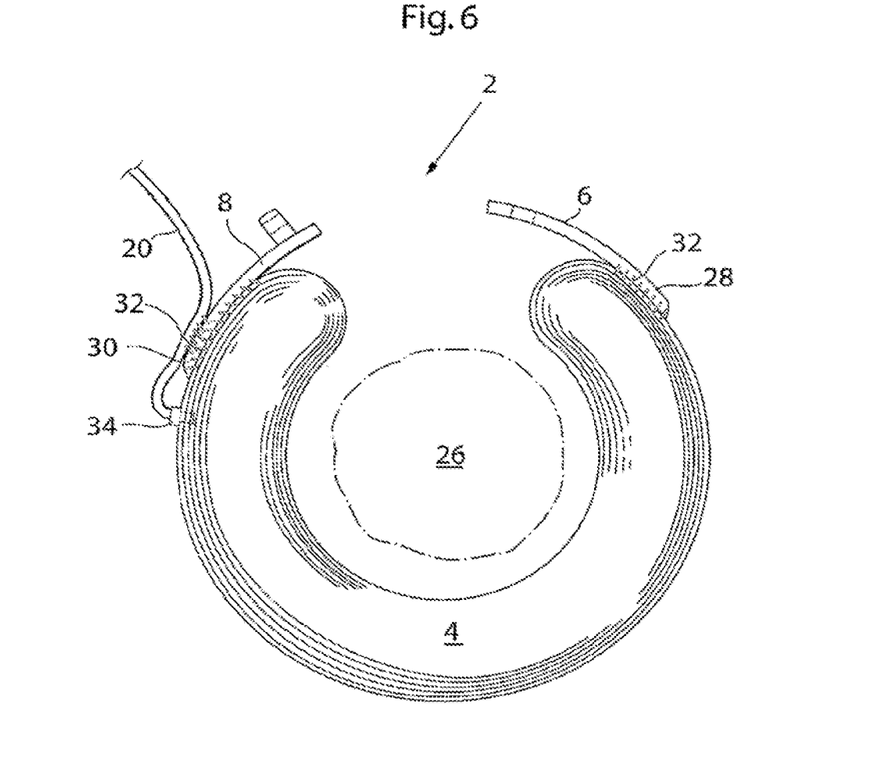
FIG. 6 shows schematically a fastening device for an implant device according to another exemplary embodiment of the invention, FIG. 7 shoves schematically a fastening device for an implant device according to a yet another exemplary embodiment of the invention.

FIG. 6 shows schematically a fastening device 2 for an implant device 4 according to another exemplary embodiment of the invention, which embodiment differs from the one described in FIG. 1, in that the film and the second fastening sections 6, 8 are arranged on separate fastening units 28, 30, and in that more than one, i.e. in this case two, of the fastening units 28, 30 are attached to the implant device 4 by attachment means 32, e.g. by chemical or mechanical means such as adhesive or suturing, and in that the implant device feed member 20 is attached to a fastening unit 30, and where the implant device feed member 20 is detachably attached to the implant device 4 via a connector device 34.

Figure 7:
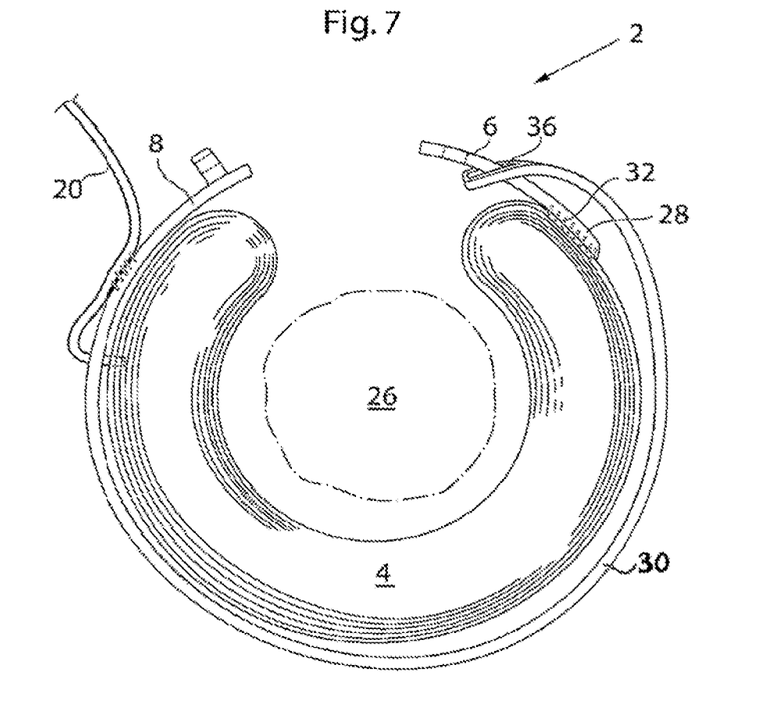

FIG. 7 shows schematically a fastening device 2 for an implant device 4 according to a yet another exemplary embodiment of the invention, which embodiment differs from the one described in FIG. 1, in that the first and the second fastening sections 6, 8 are arranged on separate fastening units 28, 30, and in that only one 28 of the fastening units 28, 30 is attached to the implant device 4 by attachment means 32, e.g. by chemical or mechanical means such as adhesive or suturing, the other fastening unit 30 having a loop 36 placed around the to the implant device 4 attached fastening unit 28, and in that the implant device feed member 20 is attached to a fastening unit 30, and where the implant device feed member 20 is non-detachably attached to the implant device 4.

FIG. 8 shows schematically fastening sections 6, 8 of a fastening device 2 according to yet another exemplary embodiment of the invention, where a first fastening section 6 is arranged with a through hole 10, a second fastening section 8 is arranged with a protruding part 12, and where said protruding part 12 is in place in said through hole 10 in a fastening device locking state (FIG. 8 shows an locked fastening device state). As can be seen from the figure, the protruding part 12 on the second fastening section 8 is arranged with a through channel 14 having an inlet 16 and an outlet 18, said through channel 14 being arranged to receive an implant device feed member 20, said inlet 16 and outlet 18 being accessible from the exterior 1, 3 of the fastening device 2 in said fastening device locking state, wherein the first fastening section 6 is securely locked to the second fastening section 8 when, in shown fastening device locking state, said implant device feed member 20 is in place in the through channel 14 and protrudes from both the inlet 16 and the outlet 1$ of said through channel 14.

The embodiment shown in FIG. 8 differs from the one described in FIG. 1, in that the inlet 16 and the outlet 18 of the through channel 14 arranged in the protruding pan 12 on the second fastening section 8 are arranged on different sides, in this case on opposite sides 1, 3, of the first fastening section 6 in the fastening device locking state. The inlet 16 of the through channel 14 arranged in the protruding part 12 on the second fastening section 8 is arranged to connect to an outlet 38 of a through hole 40 arranged in the second fastening section 8, wherein the inlet 16 of the through channel 14 arranged in the protruding part 12 on the second fastening section 8 and the outlet 18 of the through channel 14 in the second fastening section 8 are arranged on different sides of the first fastening, section 6 in the fastening device locking state.

As seen in the figure, the through channel 14 does not have to be linear, in this embodiment the through channel 14 is bent in order to arrange the inlet 16 of the through channel 14 arranged in the protruding part 12 on the second fastening section 8 adjacent to the surface of the first fastening section 6 in the fastening device locking state for minimizing any play in the locking device between the first fastening section 6 and the second fastening section 8. This may also be achieved by arranging; a depression 44 in the surface of the first fastening section 6, thereby providing a "channel" for the implant device feed member 20 in said surface. A combination of these two separate embodiments is shown in the figure.

Figure 9:
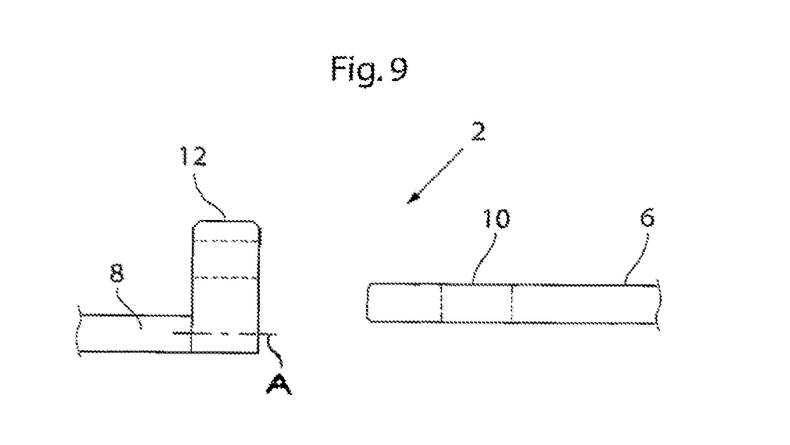
FIG. 9 shows schematically fastening sections of a fastening device according to yet another exemplary embodiment of the invention.

FIG. 9 shows schematically fastening sections 6, 8 of a fastening device 2 according to yet another exemplary embodiment of the invention, where the embodiment shown in FIG. 9 differs from the one described in FIG. 2, in that the protruding part 12 arranged on the second fastening section 8 is arranged to protrude substantially perpendicular to the longitudinal axis A of the second fastening section 8, and from one end of the second fastening section 8.

Figure 10:
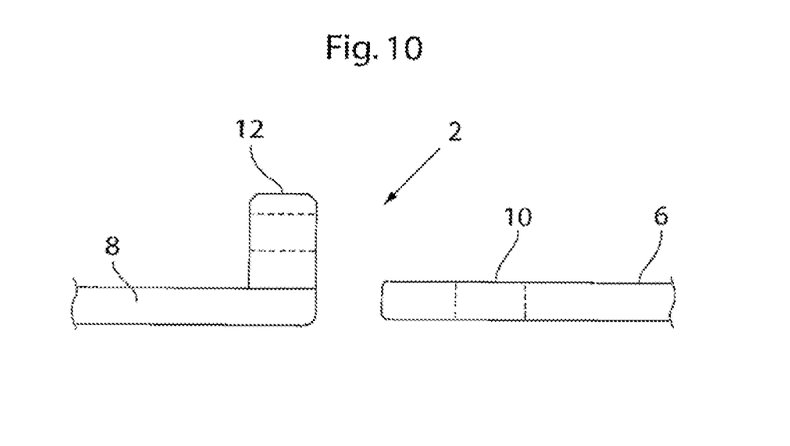
FIG. 10 shows schematically fastening sections of a fastening device according to yet another exemplary embodiment of the invention.

FIG. 10 shows schematically fastening sections 6, 8 of a fastening device 2 according, to yet another exemplary embodiment of the invention, where the embodiment shown in FIG. 10 differs from the one described in FIG. 2, in that the protruding part 12 arranged on the second fastening section 8 is arranged adjacent to one end of the second fastening section 8.

Figure 11:
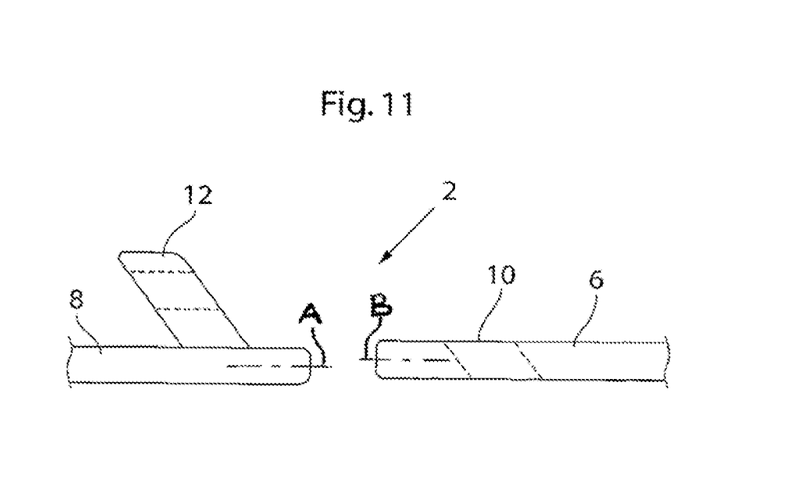
FIG. 11 shows schematically fastening sections of a fastening device according to yet another exemplary embodiment of the invention.

FIG. 11 shows schematically fastening sections 6, 8 of a fastening device 2 according to yet another exemplary embodiment of the invention, where the embodiment shown in FIG. 11 differs from the one described in FIG. 2, in that the through hole 10 arranged in the first fastening section 6 is arranged at an angle to the longitudinal axis B of the first fastening section 6 that the protruding part 12 arranged on the second fastening section 8 is arranged at an angle to the longitudinal axis A of the second fastening section 8.

Figure 12:
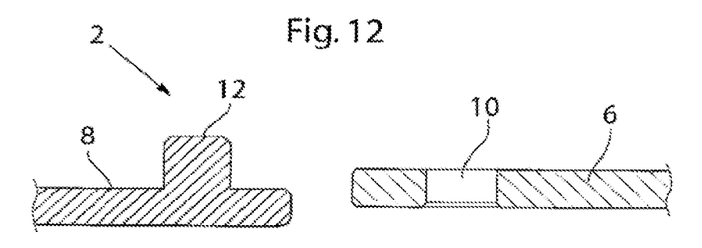
FIG. 12 shows schematically fastening sections of a fastening device according to yet another exemplary embodiment of the invention.

FIG. 12 shows schematically fastening sections 6, 8 of a fastening device 2 according to yet another exemplary embodiment of the invention, where the embodiment shown in FIG. 12 differs from the one described in FIG. 2, in that the protruding part 12 is an integrated part of the second fastening section 8.

Figure 13:
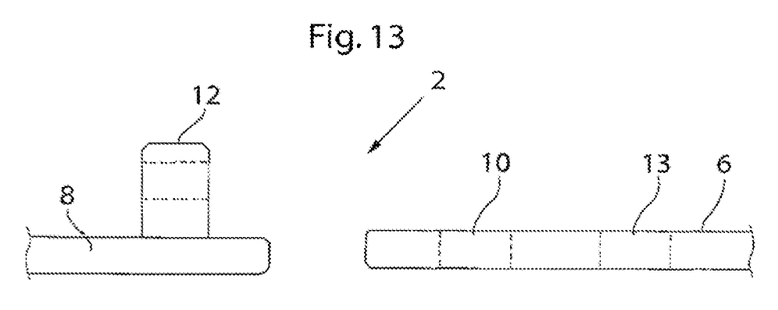
FIG. 13 shows schematically fastening sections of a fastening device according to yet another exemplary embodiment of the invention.

FIG. 13 shows schematically fastening sections 6, 8 of a fastening device 2 according to yet another exemplary embodiment of the invention, where the embodiment shown in FIG. 13 differs from the one described in FIG. 2, in that the first fastening section 6 is arranged with more than one through hole 10, 13 in order to be able to lock the fastening device 2 in more than one fastening device locking state.

Figure 14:
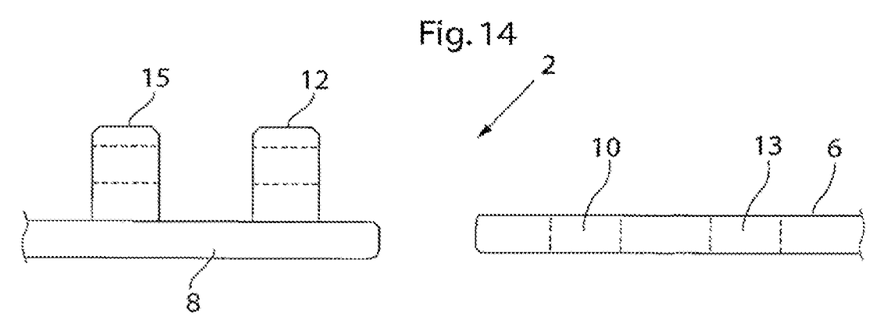
FIG. 14 shows schematically fastening sections of a fastening device according to yet another exemplary embodiment of the invention.

FIG. 14 shows schematically fastening sections of a fastening device according to yet another exemplary embodiment of the invention, where the embodiment shown in FIG. 14 differs from the one described in FIG. 2, in that the first fastening section 6 is arranged with more than one through hole 10, 13, and in that the second fastening section 8 is arranged with more than one protruding pan 12, 15 in order to be able to lock the fastening device 2 in more than one fastening device locking state, i.e. the fastening device 2 is adapted to create two or more locking positions, said fastening device 2 comprising two or more protruding parts 12, 15 and two or more through going holes 10, 13, wherein a first through going hole 10 is placed more distal to the second or more through going hole 13 to include anyone of the protruding parts 12, 15 inside said first through going hole 10, thus creating two or more locking positions.

Figure 15:
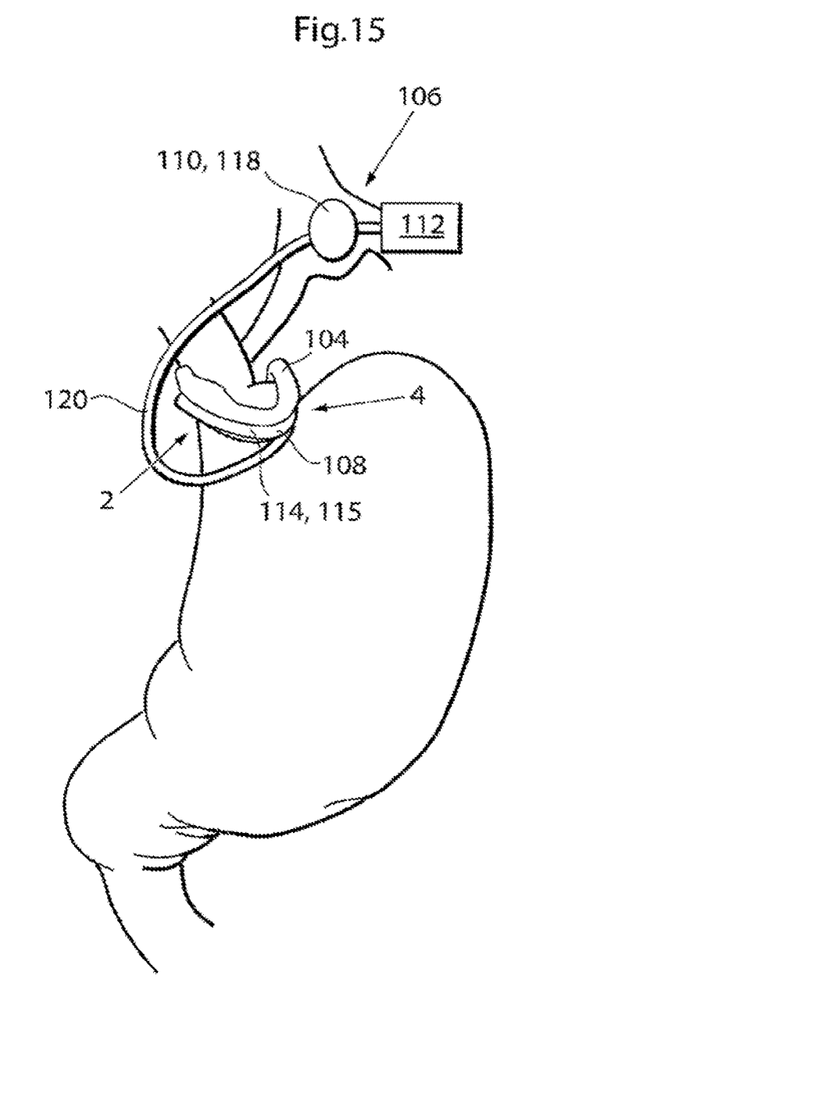
FIG. 15 shows schematically an implant device according to yet another exemplary embodiment of the invention.

FIG. 15 shows schematically an implant device according to yet another exemplary embodiment of the invention. The invention also relates to a fastening device 2, wherein the implantable implant device 4 comprises a restriction device 104 and wherein the fastening device 2 is adapted to create a closed loop by fastening said restriction device 104. The invention also relates to a fastening device 2, wherein the implant device 4 comprises at least two implant device parts 106, 108 placed remote from each other, and wherein said implant device feed member 20 is adapted to be connected to at least said two parts 106, 108, when said implant 4 is implanted in a mammal body. The invention also relates to a fastening device 2, wherein at least one of said implant device parts 106, 108 optionally comprises an internal energy source 110. The invention also relates to a fastening device 2, wherein at least one of said implant device parts 106, 108 optionally comprises an internal wireless energy receiver 112 adapted to receive wireless energy for supplying energy to any of the energy consuming parts of said implant device 4. The invention also relates to a fastening device 2, wherein at least one of said implant device parts 106, 108 optionally comprises a pump 114. The invention also relates to a fastening device 2, wherein at least one of said implant device parts 106, 108 optionally comprises a motor 115. The invention also relates to a fastening device 2, wherein said implant device 4 is an adjustable electrically powered implant device 4, comprising a restriction device 104, and a power supply 118 for powering an adjustment of said restriction device 104, wherein said fastening device 2 is adapted to fasten said first and second fastening sections 106, 108 included in said restriction device 104 into a closed loop and wherein said restriction device 104 and said power supply 118 is electrically connected by a electric cable 120, wherein said cable 120 comprising the implant feed member 20.

Figure 16:
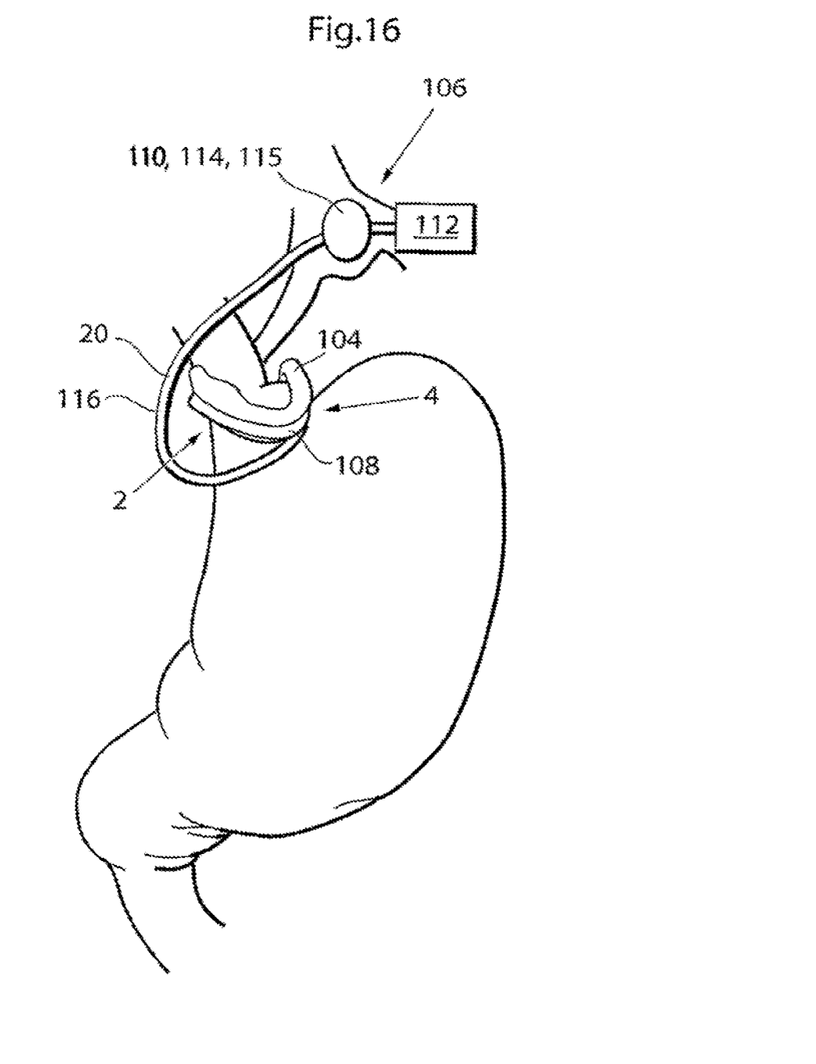
FIG. 16 shows schematically an implant device according to yet another exemplary embodiment of the invention.

FIG. 16 shows schematically an implant device according to yet another exemplary embodiment of the invention. The invention also relates to a fastening device 2, wherein the implantable implant device 4 comprises a restriction device 104 and wherein the fastening device 2 is adapted to create a closed loop by fastening said restriction device 104. The invention also relates to a fastening device 2, wherein the implant device 4 comprises at least two implant device parts 106, 108 placed remote from each other, and wherein said implant device feed member 20 is adapted to be connected to at least said two parts 106, 108, when said implant 4 is implanted in a mammal body. The invention also relates to a fastening device 2, wherein at least one of said implant device parts 106, 108 optionally comprises an internal energy source 110. The invention also relates to a fastening device 2, wherein at least one of said implant device parts 106, 108 optionally comprises an internal wireless energy receiver 112 adapted to receive wireless energy for supplying energy to any of the energy consuming parts of said implant device 4. The invention also relates to a fastening device 2, wherein at least one of said implant device parts 106, 108 optionally comprises a pump 114. The invention also relates to a fastening device 2, wherein at least one of said implant device parts 106, 108 optionally comprises a motor 115. The invention also relates to a fastening device 2, wherein said implant device 4 is an adjustable hydraulically implant device, comprising, a restriction device 104, and a pump 114 for moving hydraulic fluid to and from said restriction device 104, wherein said fastening device 2 is adapted to fasten said first and second fastening sections 106, 108 included in said restriction device 104 into a closed loop and wherein said restriction device 104 and said pump 114 is hydraulically connected by a hydraulic tube 116, wherein said tube 116 comprises the implant feed member 20.

The invention further relates to a method for securely locking a first fastening section 6 of a fastening device 2 for an implant device 4 to a second fastening section 8 of a fastening device 2 for an implant device 4, the fastening device 2 comprising at least two fastening sections 6, 8, where the first fastening section 6 is arranged with a through hole 10 and the second fastening section 8 is arranged with a protruding part 12, and where a fastening device locking state is defined by said protruding part 12 being placed in place in said through hole 10, where the method comprises the steps of:

arranging, on the protruding part 12 on the second fastening section 8, a through channel 14 having an inlet 16 and an outlet 18, said through channel 14 being arranged to receive an implant device feed member 20, said inlet 16 and outlet 18 being accessible from the exterior 1, 3 of the fastening device 2 in said fastening device locking state, placing said implant device feed member 20 in the through channel 14, and securely locking the first fastening section 6 to the second fastening section 8 by arranging, in said fastening device locking state, said implant device feed member 20 to protrude from both the inlet 16 and the outlet 18 of said through channel 14.

The invention also relates to an operation method for implanting a medical implant comprising a fastening device according to claim 1, the method comprising the steps of inserting a needle or tube-like instrument into a cavity of said mammal patient;

inflating said cavity by introducing a fluid through said needle or tube-like instrument and thereby expanding said cavity;

placing at least two laparoscopic trocars in said cavity;

inserting a camera through one of said laparoscopic trocars into said cavity;

inserting at least one dissecting tool through one of said at least two laparoscopic trocars;

dissecting an area of the body;

placing the implant with the fastening device in the dissected area;

locking a first fastening section of a fastening device for the implant device to a second fastening section of the fastening device, the fastening device comprising at least two fastening sections, where the first fastening section is arranged with a through hole and the second fastening section is arranged with a protruding part, and where a fastening device locking state is defined by said protruding part being placed in place in said through hole, arranging, on the protruding part on the second fastening section, a through channel having an inlet and an outlet, said through channel being arranged to receive an implant device feed member, said inlet and outlet being accessible from the exterior of the fastening device in said fastening device locking state, placing said implant device feed member in the through channel, and securely locking the first fastening section to the second fastening section by arranging, in said fastening device locking state, said implant device feed member to protrude from both the inlet and the outlet of said through channel, The invention also relates to an for implanting a medical implant comprising a fastening device according to claim 1, the method comprising the steps of cutting the skin of said human patient;

dissecting an area of body;

placing the implant in the dissected area;

locking a first fastening section of a fastening device for the implant device to a second fastening section of the fastening device, the fastening device comprising at least two fastening sections, where the first fastening section is arranged with a through hole and the second fastening section is arranged with a protruding part, and where a fastening device locking state is defined by said protruding part being placed in place in said through hole, arranging, on the protruding part on the second fastening section, a through channel having inlet and an outlet, said through channel being arranged to receive an implant device feed member, said inlet and outlet being accessible from the exterior of the fastening device in said fastening device locking state, placing said implant device feed member n the through channel, and securely locking the first fastening section to the second fastening section by arranging, in said fastening device locking state, said implant device feed member to protrude from both the inlet and the outlet of said through channel.

The invention also relates to a method of treating a mammal patient according to any one of above described operation methods, further comprising the step of withdrawing the instruments.

The invention also relates to a method of treating a mammal patient according to any one of above described operation methods, further comprising the step of closing the skin using sutures or staples.

The invention also relates to a method of treating a mammal patient according to any one of above described operation methods, wherein the step of dissecting includes dissecting an area of the abdomen or thorax or retroperitoneal space or pelvic region, comprising, dissecting an area of at least one of the following organs esophagus, stomach, intestine, colon, rectum, anus, anal spincter, cardia sphincter, pylori sphincter, urethra, ureter, urine bladder, vas deferens, uterine tube, blood vessel, and heart.

The invention also relates to a method of treating a mammal patient according to any one of above described operation methods, wherein the implantable device comprise a restriction device and the fastening device is adapted to create a closed loop by fastening said restriction device, wherein the method comprising the step of fastening said fastening device creating a closed loop.

The invention also relates to an implant device 4 comprising a fastening device 2 as described in any of the above embodiments, or possible combinations thereof.

Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. A method for securely locking a first fastening section of a fastening device for an implant device to a second fastening section of the fastening device, the fastening device comprising at least two fastening sections, where the first fastening section is arranged with a through hole and the second fastening section is arranged with a protruding part, and where a fastening device locking state is defined by said protruding part being placed in place in said through hole, wherein said protruding part of the second fastening section comprises a through channel having an inlet and an outlet, said through channel being arranged to receive an implant device feed member, said inlet and outlet being accessible from the exterior of the fastening device in said fastening device locking state, the method comprising the steps of:
placing said implant device feed member in the through channel, and
securely locking the first fastening section to the second fastening section by arranging, in said fastening device locking state, said implant device feed member to protrude from both the inlet and the outlet of said through channel.

2. The method according to claim 1, wherein the first fastening section has a cylindrical, tubular or band shaped cross-section.

3. The method according to claim 2, wherein the first fastening section has a tubular cross-section, and that the through hole is arranged at least through one wall of the tubular first fastening section.

4. The method according to claim 1, wherein the second fastening section has a cylindrical, tubular or band shaped cross-section.

5. The method according to claim 1, wherein the first and the second fastening sections are arranged on a fastening unit.

6. The method according to claim 5, wherein the fastening unit is attached to the implant device.

7. The method according to claim 5, wherein the implant device feed member is attached to the fastening unit.

8. The method according to claim 1, wherein the first and the second fastening sections are arranged on separate fastening units.

9. The method according to claim 8, wherein at least one of the fastening units is attached to the implant device.

10. The method according to claim 8, wherein the implant device feed member is attached to a fastening unit.

11. The method according to claim 1, wherein the inlet and the outlet of the through channel arranged in the protruding part on the second fastening section are arranged on the same side of the first fastening section in the fastening device locking state.

12. The method according to claim 1, wherein the inlet and the outlet of the through channel arranged in the protruding part on the second fastening section are arranged on different sides of the first fastening section in the fastening device locking state.

13. The method according to claim 1, wherein the outlet of the through channel arranged in the protruding part on the second fastening section is arranged to connect to an inlet of a through hole arranged in the second fastening section, wherein the inlet of the through channel arranged in the protruding part on the second fastening section and the outlet of the through hole in the second fastening section are arranged on different sides of the first fastening section in the fastening device locking state.

14. The method according to claim 13, wherein the inlet and the outlet of the through channel arranged in the protruding part on the second fastening section are arranged on opposite sides of the first fastening section in the fastening device locking state.

15. The method according to claim 1, wherein the inlet and the outlet of the through channel arranged in the protruding part on the second fastening section are arranged adjacent the surface of the first fastening section in the fastening device locking state.

16. The method according to claim 1, wherein the protruding part arranged on the second fastening section is arranged to protrude substantially axially from one end of the second fastening section.

17. The method according to claim 16, wherein the inlet and the outlet of the through channel arranged in the protruding part on the second fastening section are arranged on different sides of the second fastening section.

18. The method according to claim 1, wherein the protruding part arranged on the second fastening section is arranged to protrude substantially perpendicular to the longitudinal axis of the second fastening section, and from one end of the second fastening section.

19. The method according to claim 1, wherein the protruding part arranged on the second fastening section is arranged to protrude substantially perpendicular to the longitudinal axis of the second fastening section.

20. The method according to claim 19, wherein the protruding part arranged on the second fastening section is arranged adjacent to one end of the second fastening section.

* * * * *